(12) United States Patent
Schoess

(10) Patent No.: US 12,611,141 B1
(45) Date of Patent: *Apr. 28, 2026

(54) EXERCISE EVALUATION AND RECOVERY THERAPY SYSTEM AND METHOD

(71) Applicant: EDEN MEDICAL, INC., Howard Lake, MN (US)

(72) Inventor: Jeffrey Norman Schoess, Howard Lake, MN (US)

(73) Assignee: EDEN MEDICAL, INC., South Haven, MN (US)

( * ) Notice: Subject to any disclaimer, the term of this patent is extended or adjusted under 35 U.S.C. 154(b) by 253 days.

This patent is subject to a terminal disclaimer.

(21) Appl. No.: 17/986,629

(22) Filed: Nov. 14, 2022

(51) Int. Cl.
*A61B 5/00* (2006.01)
*A61B 5/1455* (2006.01)

(52) U.S. Cl.
CPC ............ *A61B 5/486* (2013.01); *A61B 5/0004* (2013.01); *A61B 5/14552* (2013.01)

(58) Field of Classification Search
None
See application file for complete search history.

(56) References Cited

U.S. PATENT DOCUMENTS

2016/0220808 A1* 8/2016 Hyde ................... A61B 5/6804
2018/0249937 A1* 9/2018 Wiese ................. A61B 5/6831

* cited by examiner

*Primary Examiner* — Benjamin S Melhus
(74) *Attorney, Agent, or Firm* — UNDERWOOD & ASSOCIATES, LLC

(57) ABSTRACT

A method for assessing and reversing exercise impairment in adults having peripheral vascular disease includes quantifying a musculoskeletal deoxygenation level (MDL) of a human subject provided by a wearable near infrared spectroscopy system configured to measure the deoxygenation level during exercise, comparing the quantified MDL to a range of pre-determined healthy MDL values for the subject, and, if the quantified MDL is outside of the pre-determined target MDL values, determining a corrective exercise intensity level or 'dose' effective to bring the MDL of the subject within the target MDL values and reverse the exercise impairment.

23 Claims, 1 Drawing Sheet

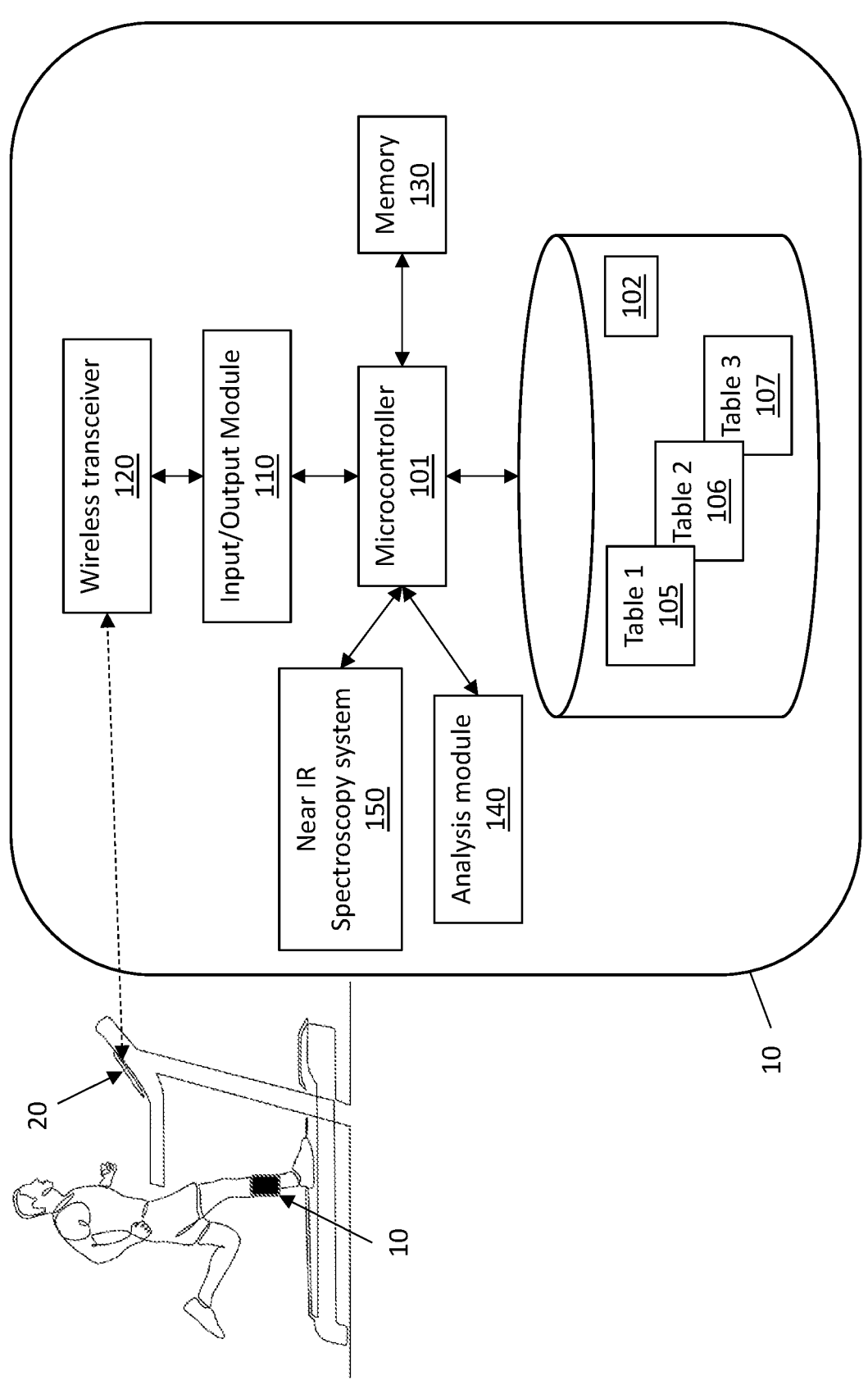

EXERCISE EVALUATION AND RECOVERY THERAPY SYSTEM AND METHOD

STATEMENT OF FEDERALLY SPONSORED RESEARCH

This invention was made with government support under Project No. 1R43AG060868-01 awarded by the National Institute on Aging. The government has certain rights in the invention.

CROSS REFERENCE TO RELATED APPLICATIONS

Continuation-in-part of U.S. application Ser. No. 17/523, 832, now U.S. Pat. No. 11,497,442, which claims priority to and the benefit under 35 USC § 119 (e) of U.S. Provisional Patent Application No. 63/111,974 filed on Nov. 20, 2020. The contents of the foregoing applications are incorporated by reference in their entirety as if fully set forth herein.

TECHNICAL FIELD

This disclosure relates to systems and methods for measuring and reversing exercise impairment of human subjects with peripheral vascular and arterial disease.

BACKGROUND OF INVENTION

Peripheral arterial disease (PAD) is a prevalent, morbid, and mortal disease. In the US, the total economic impact of PAD in 2010 was $392 billion. The majority of the cost was for hospitalization costs at $344 billion (i.e. 88% of the total). In 2015, the economic burden of PAD exceeded that of diabetes, coronary artery disease and all cancers. The traditional risk factors for PAD include cigarette smoking, diabetes mellitus, hypertension, dyslipidemia, and obesity. The risk of intermittent claudication is about twice as high in patients with diabetes as in individuals without diabetes.

The risks of PAD increase with the severity of diabetes: for every 1% increase in hemoglobin A1c level, the risk of PAD increases by 26%. Better control of PAD can reduce cost, increase quality of life and decrease mortality rate.

The most common symptom of PAD is muscle pain in the lower limbs on exercise (intermittent claudication). Walking impairment occurs with fatigue, aching, cramping or pain in the buttock, thigh, calf or foot, particularly when symptoms are quickly relieved at rest. Pain comes on more rapidly when walking uphill than on the flat. Claudication can occur in both legs but is often worse in one leg. The potential biomechanical or biochemical mechanisms underlying the benefits of exercise therapy for PAD are exercise-induced angiogenesis, enhanced nitric oxide-dependent vasodilatation of the microcirculation, improved hemorheology, reduced vascular inflammation, improved glucose and fatty acid metabolism in skeletal muscle, improved muscle bioenergetics and oxidative stress, and improved peripheral nerve function.

The mechanisms underlying the response to exercise therapy include improvements in blood perfusion, muscle metabolism and mitochondrial function, peripheral nerve function, and walking efficiency. It is well established that exercise is effective for treating claudication among patients with PAD; however, many PAD patients avoid engaging in regular exercise because of fear-avoidance beliefs that exercise may worse their pain condition. This could be because of lack of a personalized tool allowing assessing/predicting patients' tolerance to perform exercise without overtaxing them.

Thus, a platform to fill this gap by providing an intuitive and objective metric predicting the tolerance of a PAD patients with intermittent claudication symptoms before reaching significant pain levels, as well as estimating the duration of needed rest before starting a new session of exercise, is an unmet need in the arts.

SUMMARY OF THE INVENTION

In general, an exercise evaluation and recovery therapy system and method are disclosed. In an exemplary embodiment, a method for assessing and reversing exercise impairment in adults having peripheral vascular disease includes quantifying a musculoskeletal deoxygenation level (MDL) of a human subject provided by a wearable near infrared spectroscopy system configured to measure the deoxygenation level during exercise, comparing the quantified MDL to a range of pre-determined healthy MDL values for the subject, and, if the quantified MDL is outside of the predetermined target MDL values, determining a corrective exercise intensity level or 'dose' effective to bring the MDL of the subject within the target MDL values and reverse the exercise impairment.

Unless otherwise defined, all technical and scientific terms used herein have the same meaning as commonly understood by one of ordinary skill in the art. Although methods and materials similar or equivalent to those described herein can be used in the practice or testing of any described embodiment, suitable methods and materials are described below. In addition, the materials, methods, and examples are illustrative only and not intended to be limiting. In case of conflict with terms used in the art, the present specification, including definitions, will control.

The foregoing summary is illustrative only and is not intended to be in any way limiting. In addition to the illustrative aspects, embodiments, and features described above, further aspects, embodiments, and features will become apparent by reference to the drawings and the following detailed description and claims.

BRIEF DESCRIPTION OF DRAWINGS

FIG. 1 is a system diagram of an exercise evaluation and recovery treatment system according to one embodiment.

DETAILED DESCRIPTION

It is well established that exercise is effective to treat claudication among patients with peripheral arterial disease (PAD); however, many PAD patients avoid engaging in regular exercise because of fear-avoidance beliefs that exercise may worse their pain condition. In general, an Exercise Evaluation and Recovery Treatment (hereinafter 'EXERT') platform is disclosed that can provide an intuitive and objective metric predicting the tolerance of PAD patients with intermittent claudication symptoms before experiencing significant pain. The EXERT platform can additionally estimate the duration of needed rest before starting a new session of exercise.

In one embodiment, an EXERT system is a mobile health (mHealth) solution for assessing exercise impairment of adult peripheral vascular disease (PVD) patients and increasing their exercise capacity. The public health problem of physical inactivity has proven resistant to research efforts aimed at elucidating its causes and personalized interventions designed to alter this cause. Most theoretical models of exercise behavior assume that the decision to engage in exercise is based on cognitive factors (e.g. weighting pros and cons).

Another, still under-appreciated possibility is that these decisions are influenced by affective variables, such as whether previous exercise experiences were associated with pleasure or displeasure. This is in particular true in older adults with peripheral arterial disease (PAD), in whom conventional exercise programs could easily overtax them and thus discourage them in engagement of future exercise. Overtaxing during exercise is believed to be highly dependent on muscle oxidative capacity and muscle deoxygenation. While this capacity could be improved by exercise intervention, it is essential to assess the capacity of the participant to avoid overtaxing and thus disengagement in continue exercise.

In this embodiment, the EXERT system includes a wearable Bluetooth enabled near infrared spectroscopy (NIRS) system to quantify skeletal muscle deoxygenation levels to assess muscle oxidative recovery between exercise sessions and avoid overtaxing participant during exercise. NIRS deoxygenation (Hb) provides a noninvasive measure of muscle oxygen extraction. The EXERT incorporates a recovery strategy to inform an exercise trainer on a capacity level of the patient and personalized exercise program to avoid overtaxing the patients and thus motivate them to engage in regular exercise to reverse the exercise impairment.

This is accomplished using an 'exercise prescription' or exercise 'dose' based on biofeedback intensity levels. The intensity level of exercise can be used as a prescription variable. The prescription could also include specific workloads (e.g., walking speed), duration and frequency of the exercise. The prescription dose could be adjusted remotely through a digital dashboard, as the therapist monitors patient performance (e.g., degree of claudication). Compliance, patient feedback and motivational incentives can be implemented via the digital dashboard.

In one embodiment, a method for assessing and reversing exercise impairment in adults having peripheral vascular disease includes quantifying a musculoskeletal deoxygenation level (MDL) of a human subject provided by a wearable near infrared spectroscopy system (NIRSS) configured to measure the deoxygenation level of the subject during exercise.

A suitable near infrared spectroscopy system can include, without limitation, a sensor board having an analog front end (AFE) integrated circuit (IC), inertial measurement unit (IMU), two near infrared LEDs and photodiodes. One suitable AFE IC is the Maxim 81641 Optical Unit provided by Maxim Integrated, San Jose, California, USA. The 81641 model features a two-channel data acquisition system, programmable LED driver (four full scale ranges, 32, 64, 93, and 124 ma) to drive the two LEDs at 730 and 850 nm respectively, two optical readout channels (two photodiode interface), first-in-first out (FIFO) memory, two 19-bit A/Ds.

The MCU board can include the microcontroller IC to acquire the data, a wireless Bluetooth interface for user interface support, built-in read only (ROM) and random-access (RAM) memory and battery management. The optical channel has 4 full scale ranges. These ranges are 4 to 32 μA. It has dual LED drivers, two photodiodes to capture the near infrared light, and SPI bus interface.

In this embodiment, LED1 can be sampled first followed by LED 2, and then a direct ambient sample can be acquired as a baseline measurement for a $HbO_2/Hb$ algorithm calculation. The clock pulse width (tpw) is a minimum of 1.0 μs.

In this embodiment, the EXERT design includes an optical interface board (dual wavelength LEDs operable at 730 nm and 750 nm, respectively, 3 light pipes and 2 photodiodes mounted in a wearable package. The package design features a concave shape to fit and effectively project NIR light into the gastrocnemius muscle centered between medial/lateral heads.

In an alternative embodiment, two near infrared LEDs and one photodiode can be used which could be time multiplexed to capture the infrared light. The benefit of this layout would be the ability to select higher optical power LEDs to increase the depth of light penetration, projecting light into the deeper into the muscle to quantify deoxygenation.

The depth of light penetration can be chosen; one optimal depth is 10 mm. The path of light propagation follows the modified Beer-Lambert Law, an arcuate path depending on light attenuation due to absorption. The Beer-Lambert law defines the depth of penetration to be one-half the distance between the light source and photodetector, so a 10 mm depth defined the source-detector distance to be set at 20 mm.

Effective penetration of light can also determined by several other factors: wavelength, attenuation coefficient (scattering, refraction, and absorption), area of irradiance (power density-watts/cm2), and light pulsing. The light pipe provides effective flux coupling projecting the light with minimum flux loss. The losses include LED insertion (Fresnel) loss (up to 4% loss,) light leakage out the pipe wall (10 to 50% loss), and pipe exit Fresnel loss (4%). The radiation pattern at the pipe exit can be designed to maximize on-axis intensity and a narrow radiation pattern with a small viewing angle.

A dual wavelength, bi-color LED (Marubeni, part no. SMT 730/850D) for development can be utilized as it features peak wavelength operation at 730 and 850 nm. The LED has a wide radiation field of +/−62 degrees to provide the best flux capture. A PIN photodiode (Vishay Semi VEMD5060X01) can be used as a surface mount device with a 7.5 mm2 sensitive area with a high responsivity of 64 mV/(microwatt/cm2).

The LED projects light in the 12 mm acrylic light pipe and into the skin/tissue of the test subject. The light is absorbed, scattered and reflected back into a second light pipe, and detected by the photodiode. An LED operating at 124 ma (310 mW) can project 1,150 mw/cm2 optical power output at the light pipe output. Taking in account the Fresnel losses, tissue loss due to scattering, reflection and absorption and light pipe return loss, the photodiode will detect 0.19 mw/cm2 of light energy.

In this embodiment, the method further includes comparing the quantified MDL to a range of pre-determined healthy MDL values for the subject. If the quantified MDL is outside of the pre-determined target MDL values, a corrective exercise intensity level can be determined that is effective to bring the MDL of the subject within the target MDL values and reverse the exercise impairment.

In this embodiment, the method can be applied to human subjects having a chronic disease such as peripheral vascular disease or peripheral arterial disease. A determination of the target MDL values can be customized based upon the chronic disease of the human subject.

Alternatively, the human subject may have a chronic disease, and a determination of the target MDL values can be customized based upon the chronic disease and one or more measured physiological factors of the human subject.

The wearable near infrared spectroscopy system can further include an electronic module configured to wirelessly transmit the measured deoxygenation level to a remote receiver during exercise. When those data are received and processed, a step in the present method can include instructing the human subject to increase or decrease an exercise intensity level if the quantified MDL value is outside of the pre-determined healthy MDL. Tables of MDL values for healthy subjects and those with particular chronic diseases may be kept, for example, in an electronic database for reference. Each chronic disease may be associated with a particular table of MDL data.

In one embodiment, the method further includes instructing the human subject to change to a different exercise if the quantified MDL value is outside of the pre-determined healthy MDL range. This can be accomplished, for example and without limitation, by a trainer, a physical therapist, an occupational therapist, a personal electronic device such as a smart phone, tablet or other known electronic device.

In one embodiment, determining a corrective exercise intensity level includes determining a modified exercise workload, duration, frequency or a combination thereof. This information can then be relayed to the subject.

In one embodiment, the wearable near infrared spectroscopy system includes an infrared light source and a detector configured to receive the infrared light source after propagating through a selected portion of the human subject's skin tissue. Non-limiting examples of preferred skin tissue includes the calf muscle, wrist or forearm.

In one embodiment, the near infrared spectroscopy system can include one or more physiological sensors, such as, but without limitation, a deoxygenation probe, an accelerometer, a pulse or pulse-less oximeter, a pulse-rate monitor, a moisture sensor, a thermometer or a combination thereof.

In a general aspect, a system for assessing and reversing exercise impairment of a human subject with adult peripheral vascular disease is disclosed. In one embodiment, the system for assessing exercise impairment includes a wearable device. The wearable device can include at least one sensor configured to measure a musculoskeletal deoxygenation level (MDL) in the human subject while exercising. For example, a sensor of the type described herein can be placed on a selected portion of tissue of the subject, such as the exterior portion of a calf muscle, wrist or forearm. The system further includes a memory configured to store a plurality of the musculoskeletal deoxygenation levels in a digital-electronic format, such as in electronic tabular form or in a relational database. The system further includes an input/output module configured for transmitting the collected musculoskeletal deoxygenation levels to a remote electronic device.

The input/output module can be, for example, a wireless transmitter utilizing, for example, Bluetooth or WiFi communication protocols. The system further includes a reference table of target musculoskeletal deoxygenation levels stored in digital-electronic format, such as in electronic tabular form or in a relational database, for example. The system further includes a processor in signal communication with the reference table, the processor being configured to compare at least one of the plurality of the musculoskeletal deoxygenation levels to the reference table. The system further includes a software module configured to determine a corrective exercise intensity level effective to bring the MDL of the subject within a target musculoskeletal deoxygenation level values while the human subject is exercising and reverse the exercise impairment In one embodiment, the input/output module includes a wireless transmitter and receiver.

In this embodiment, the sensor is a near infrared spectroscopy system as described herein. The wearable device can further include one or more physiological sensors in addition to the near infrared spectroscopy system. The one or more physiological sensors can be for example, and without limitation, an accelerometer, an oximeter, a pulse-rate monitor, a moisture sensor, a thermometer or a combination thereof.

In this embodiment, the reference table of target musculoskeletal deoxygenation levels comprises musculoskeletal deoxygenation levels representative of a healthy human subject. The reference table of target musculoskeletal deoxygenation levels can include musculoskeletal deoxygenation levels representative of a human subject having a chronic illness, such as peripheral vascular disease or peripheral arterial disease.

Referring now to FIG. 1, a system diagram of an exercise evaluation and recovery treatment system 10 is shown according to one embodiment. The system 10 is shown embodied as a wearable device, in this example, attached to the calf of a human who is exercising. In this embodiment, the system 100 includes a microcontroller 101 in signal communication with an electronic data repository 102 of tables 105, 106, 107, an input/output module 110, a wireless transceiver 120, a memory module 130, an analysis module 140 and a near-IR spectroscopy system 150.

In this embodiment, the microcontroller 101 is configured to carry out software instructions, which may be stored, e.g., in memory module 130, for acquiring a MDL measurement of the exercising subject via the near-IR spectroscopy system 150. The near-IR spectroscopy system can be, e.g., that described herein. After an MDL measurement has been acquired, that measurement can be compared by the analysis module 140 to various tables (105, 106, 107) of healthy MDL values in data repository 102. Data repository 102 can be, e.g., a relational database such as a MySQL database. The various tables 105, 106, 107 can include, e.g., data representing target MDL values for a particular disease, MDL values of healthy subjects or target MDL values prescribed a physician or therapist.

In this embodiment, the analysis module 140 compares the measured MDL value of the subject against the MDL values of a table in the repository 102. If the measured MDL level is out of range of the MDL values stored in a particular table or tables, a corrective instruction is sent to the input/output module 110. The input/output module 110, which can include, e.g., a wireless Bluetooth transceiver, can cause the wireless transceiver 120 to send a signal to a device interface 20, which is placed in view of the exercising subject. The subject can then adjust their exercise, e.g., intensity level, so that their measured MDL falls within an acceptable range as defined in the tables of the repository 102. The system 10 can repeat the measurement and analysis step at a selected acquisition rate, e.g., once every 30 seconds, so that the subject sees real-time feedback from the system 10 and can adjust exercise accordingly. Subject MDL data can be stored in repository 102 and transmitted to a physician or therapist for monitoring and/or adjustment of the MDL tables particular to the subject's exercise and recovery regimen.

A number of illustrative embodiments have been described. Nevertheless, it will be understood that various modifications may be made without departing from the spirit and scope of the various embodiments presented herein. Accordingly, other embodiments are within the scope of the following claims.

The invention claimed is:

1. A system for assessing and reversing exercise impairment of a human subject with adult peripheral vascular disease, comprising:
    a wearable near-infrared spectroscopy system comprising:
        at least two near-infrared light sources and at least two detectors configured to receive said infrared light after propagating through a selected portion of said human subject's soft tissue and determine a musculoskeletal deoxygenation level (MDL) in said human subject while exercising; wherein one of said near-infrared light sources comprises a first LED emitting at about 730 nm and a second LED emitting at about 850 nm, and wherein said wearable near-infrared spectroscopy system further comprises a microcontroller having an analog front-end and a memory programmed to sequentially sample the first LED, the second LED, and an ambient baseline and to compute said MDL by applying a Beer-Lambert algorithm;
        a memory configured to store a plurality of said musculoskeletal deoxygenation levels in a digital-electronic format;
        an input/output module comprising a wireless transceiver configured to wirelessly transmit a machine-readable corrective exercise-intensity instruction to a display device interface of, or attached to an exercise machine, the display device interface being positioned in view of said human subject during an exercise session;
        a reference table of target musculoskeletal deoxygenation levels stored in digital-electronic format;
        a processor in signal communication with said memory, said input/output module, and the reference table, said processor being configured to compare at least one of said determined plurality of said musculoskeletal deoxygenation levels to said reference table, and to generate, in real time, said machine-readable corrective exercise-intensity instruction when said determined MDL lies outside a target MDL range; and
        an analysis module comprising at least one processor configured to execute stored program instructions to determine a real-time corrective exercise intensity level effective to bring said MDL of said subject within said target musculoskeletal deoxygenation level values while said human subject is exercising and reverse said exercise impairment;
        the analysis module being executed by the processor to supply the machine-readable corrective exercise-intensity instruction to the electronic module for immediate wireless transmission;
        wherein said human subject has a chronic disease, and wherein said target range of musculoskeletal deoxygenation level values are pre-determined based on said chronic disease and stored in said reference table; and
        wherein the target MDL range is stored before the exercise session and is derived from musculoskeletal deoxygenation data collected from patients diagnosed with peripheral vascular disease.

2. The system of claim 1, wherein said input/output module comprises a wireless transmitter and receiver.

3. The system of claim 1, wherein said wearable device further comprises one or more physiological sensors in addition to said near infrared spectroscopy system.

4. The system of claim 3, wherein said one or more physiological sensors is an accelerometer, a heart variability rate sensor, an oximeter, a heart rate monitor, a moisture sensor, a thermometer or a combination thereof.

5. The system of claim 1, wherein said target range of musculoskeletal deoxygenation levels is pre-determined based on healthy human subjects, adjusted for said human subject's chronic disease and one or more measured physiological factors.

6. The system of claim 1, wherein said reference table of target musculoskeletal deoxygenation levels comprises musculoskeletal deoxygenation levels representative of a human subject having a chronic illness.

7. The system of claim 6, wherein said chronic illness is peripheral vascular disease, peripheral arterial disease or metabolic muscle disease.

8. A method for assessing exercise impairment in a patient having a chronic disease, comprising:
    measuring a musculoskeletal deoxygenation level (MDL) of said patient during exercise by sequentially:
        (i) illuminating a selected portion of the patient's soft tissue with a first near-infrared LED emitting at about 730 nm,
        (ii) illuminating the selected portion with a second near-infrared LED emitting at about 850 nm, and
        (iii) acquiring an ambient baseline sample, and (iv) computing the MDL by applying a Beer-Lambert calculation to the sequential samples;
    electronically comparing said measured musculoskeletal deoxygenation level (MDL) to a digitally encoded range of pre-determined target MDL values for said patient, said values being stored in a non-transitory memory device; and
    determining an effective dose of a corrective exercise intensity level, said effective dose comprising a modified exercise workload, duration, frequency, or a combination thereof, if said measured MDL is outside of said target MDL values; and
    wirelessly transmitting, via a wireless transceiver, a machine-readable corrective exercise-intensity instruction to a display device interface of an exercise machine, the display device interface being positioned in view of said patient in real time, thereby enabling the patient to adjust exercise workload in real time, during the same exercise session;
    wherein the range of pre-determined target MDL values are stored before the exercise session and is derived from musculoskeletal deoxygenation data collected from patients diagnosed with peripheral vascular disease.

9. The method of claim 8, wherein said chronic disease is peripheral vascular disease, peripheral arterial disease or metabolic muscle disease.

10. The method of claim 8, wherein said corrective exercise intensity level is effective to bring the MDL of said subject within said range of target MDL values.

11. The method of claim 8, further comprising transmitting said determined corrective exercise intensity level to said patient or a clinician overseeing said patient's exercise level.

12. The method of claim 8, wherein said measuring a (MDL) of said patient during exercise is accomplished by a wearable near-infrared spectroscopy system, said wearable near infrared spectroscopy system comprising an infrared light source and a detector configured to receive said infrared light after propagating through a selected portion of said patient's soft tissue.

13. The method of claim 12, wherein:

said wearable near infrared spectroscopy system comprises at least one probe light source; and wherein said wearable near infrared spectroscopy system is configured to be worn around an appendage of said subject such that said at least one probe light source directs light into a selected portion of said subject's soft tissue.

14. The method of claim 13, wherein said near infrared spectroscopy system further comprises a detector configured to detect light from said light source after propagating through said selected portion of said subject's soft tissue.

15. The method of claim 8, wherein said determining said corrective exercise intensity level comprises determining a corrective exercise workload, duration, or frequency.

16. A system for assessing and reversing exercise impairment of a human subject with a chronic disease, comprising:

a wearable probe and sensor combination configured to measure a muscle deoxygenation level (MDL) of said subject while exercising, the wearable probe and sensor combination comprising:

(i) a first near-infrared LED emitting at about 730 nm, (ii) a second near-infrared LED emitting at about 850 nm, (iii) at least one photodiode detector, and (iv) a microcontroller having an analog front-end with FIFO memory programmed to sequentially sample the first LED, the second LED and an ambient baseline and to compute said MDL by applying a Beer-Lambert algorithm;

a non-transitory memory device storing a digitally encoded range of pre-determined musculoskeletal deoxygenation level (MDL) values for said subject, said range being pre-determined based on said subject's chronic disease;

a processor in signal communication with said non-transitory memory device, said processor configured to retrieve each computed MDL at a sampling interval of about thirty seconds, compare said measured musculoskeletal deoxygenation level (MDL) values to said digitally encoded target range, and to generate, in real-time, a machine-readable corrective exercise intensity instruction effective to bring said measured MDL of said subject within said target range of MDL values in real-time while exercising; and an input/output module in signal communication with said processor configured to transmit the machine-readable corrective exercise-intensity instruction, the input/output module comprising a wireless transceiver configured to transmit the instruction to a display device interface of an exercise machine, the display device interface being positioned in view of said subject during the exercise session; and wherein the target range of MDL values is stored before the exercise session and is derived from musculoskeletal deoxygenation data collected from patients diagnosed with peripheral vascular disease.

17. The system of claim 16, wherein said target healthy MDL values accounts for said chronic disease of said subject.

18. The system of claim 16, wherein said probe and sensor combination comprises a near infrared spectroscopy system.

19. The system of claim 16, wherein said chronic disease is peripheral vascular disease, peripheral arterial disease, or metabolic muscle disease.

20. The system of claim 16, wherein said corrective exercise intensity level is transmitted to said subject or a clinician overseeing said subject, so as to cause said subject to change exercise workload, duration, or frequency.

21. The system of claim 1 wherein said analysis module is further configured to determine a corrective exercise intensity level effective to increase the exercise capacity of said human subject.

22. The method of claim 8, wherein said corrective exercise intensity level is selected to increase exercise capacity of said patient.

23. The system of claim 16, wherein said corrective exercise intensity level is further effective to increase the exercise intensity level of said human subject.

\* \* \* \* \*